US010871363B2

(12) United States Patent
Yuan et al.

(10) Patent No.: US 10,871,363 B2
(45) Date of Patent: Dec. 22, 2020

(54) ORAL CARE COMPOSITION WITH IMPROVED DEPOSITION EFFICACY OF A COOLING SENSATE AGENT IN THE ORAL CAVITY

(71) Applicant: The Procter & Gamble Company, Cincinnati, OH (US)

(72) Inventors: Jinfang Yuan, Beijing (CN); Yan Zhang, Beijing (CN); Xiaowei Li, Beijing (CN); Ross Strand, Singapore (SG)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 16/423,732

(22) Filed: May 28, 2019

(65) Prior Publication Data
US 2019/0358139 A1 Nov. 28, 2019

(30) Foreign Application Priority Data

May 28, 2018 (WO) ................ PCT/CN2018/088642

(51) Int. Cl.
A61K 8/19 (2006.01)
G01B 5/00 (2006.01)
G01B 5/08 (2006.01)
G01M 13/04 (2019.01)
A61K 8/21 (2006.01)
A61K 8/24 (2006.01)
A61K 8/25 (2006.01)
A61K 8/34 (2006.01)
A61K 8/42 (2006.01)
A61K 8/73 (2006.01)
A61K 8/81 (2006.01)
A61Q 11/00 (2006.01)

(52) U.S. Cl.
CPC .............. G01B 5/0025 (2013.01); A61K 8/19 (2013.01); A61K 8/21 (2013.01); A61K 8/24 (2013.01); A61K 8/25 (2013.01); A61K 8/345 (2013.01); A61K 8/347 (2013.01); A61K 8/42 (2013.01); A61K 8/73 (2013.01); A61K 8/731 (2013.01); A61K 8/8147 (2013.01); A61Q 11/00 (2013.01); G01B 5/08 (2013.01); G01M 13/04 (2013.01)

(58) Field of Classification Search
None
See application file for complete search history.

(56) References Cited

U.S. PATENT DOCUMENTS

| | | |
|---|---|---|
| 4,136,163 A | 1/1979 | Watson |
| 4,178,459 A | 12/1979 | Rowsell |
| 7,189,760 B2 | 3/2007 | Erman |
| 7,414,152 B2 | 8/2008 | Galopin |
| 8,426,643 B2 | 4/2013 | Yelm |
| RE44,339 E | 7/2013 | Galopin et al. |
| 8,754,259 B2 | 6/2014 | Yelm |
| 8,853,267 B2 | 10/2014 | Wei |
| 9,186,306 B2 | 11/2015 | Midha |
| 9,549,887 B2 | 1/2017 | Midha |
| 9,918,915 B2 | 3/2018 | Haught |
| 9,949,907 B2 | 4/2018 | D'ambrogio |
| 9,974,723 B2 | 5/2018 | D'ambrogio |
| 10,231,910 B2 | 3/2019 | Lei |
| 2008/0227857 A1 | 9/2008 | Wei |
| 2010/0086498 A1 | 4/2010 | Haught |
| 2011/0082204 A1 | 4/2011 | Wei |
| 2011/0160303 A1 | 6/2011 | Wei |
| 2012/0082628 A1* | 4/2012 | Haught .................. A61K 8/37 424/51 |
| 2013/0224270 A1 | 8/2013 | Robinson |
| 2014/0186272 A1 | 7/2014 | Yelm |
| 2017/0014321 A1 | 1/2017 | D'ambrogio |
| 2017/0281486 A1 | 10/2017 | Midha |
| 2018/0289598 A1 | 10/2018 | Potnis |

FOREIGN PATENT DOCUMENTS

WO WO2017167535 A1 10/2017

* cited by examiner

Primary Examiner — Nannette Holloman
(74) Attorney, Agent, or Firm — Jason J. Camp

(57) ABSTRACT

Oral care composition for increasing deposition efficacy of a cooling sensate agent in the oral cavity. The oral care composition is made up of water and a calcium-containing abrasive to form a calcium-containing abrasive based carrier, and a cooling sensate agent comprising a N-substituted p-menthanecarboxamide containing compound.

22 Claims, No Drawings

ORAL CARE COMPOSITION WITH IMPROVED DEPOSITION EFFICACY OF A COOLING SENSATE AGENT IN THE ORAL CAVITY

FIELD OF THE INVENTION

The present invention relates to oral care compositions having cooling sensate agents for providing freshness benefits. More particularly, the present invention relates to an oral care composition with improved deposition efficacy of a cooling sensate agent in the oral cavity and a method of increasing deposition of N-substituted p-menthanecarboxamide containing compound on a surface of the oral cavity.

BACKGROUND OF THE INVENTION

Cooling sensate agents that have a physiological cooling and/or freshening effect on oral and other mucosal surfaces and skin are common ingredients in a wide variety of products. Such products include for example, mouthwashes, dental and throat lozenges, gargles, chewing gum, dentifrice or toothpastes, toothpicks, dental tablets and powders and topical solutions for application in dental treatment. In particular, oral care products such as dentifrices are formulated with cooling sensate agents because they provide breath freshening effects and a clean, cool, and fresh feeling in the mouth. The pleasant cooling sensation provided by cooling sensate agents contributes to the appeal and acceptability of the products.

Known cooling sensate agents include 1-menthol which is found naturally in peppermint oil. However, 1-menthol is volatile and hence although it has a strong cooling and/or refreshing effect, the effect is not long-lasting, i.e. the duration of freshness is short. Therefore, there is a high demand for coolant compounds with high cooling potency and long-lasting cooling effect. Such coolant compounds are described for example in International Publication No. WO2005/049553A1 to Givaudan S. A. However, such coolant compounds are relatively expensive and including such compounds in high levels when formulating products increase costs.

Accordingly, there remains a need to provide a cost-effective oral composition that provides a long-lasting freshness effect.

SUMMARY OF THE INVENTION

The present invention relates to an oral composition comprising:
(a) 20% to 75%, by weight of the composition, of water,
(b) a calcium-containing abrasive, and
(c) 0.001% to 0.02%, by weight of the composition, of a cooling sensate agent comprising a N-substituted p-menthanecarboxamide containing compound.

DETAILED DESCRIPTION OF THE INVENTION

Cooling sensate agents are typically formulated with an orally acceptable carrier for topical oral administration. Carrier materials that make up the orally acceptable carrier are chosen in light of the way the composition is to be introduced into the oral cavity. Carrier materials suitable for dentifrice compositions or toothpaste typically include abrasive materials, water to prevent the toothpaste from drying out, humectants to help prevent water loss in the toothpaste, and thickening agents to stabilize the toothpaste formulation.

The present invention is based on the surprising discovery that the oral composition of the present invention (hereinafter "composition") comprising a calcium-containing abrasive based carrier and relatively low levels of a cooling sensate agent having a N-substituted p-menthanecarboxamide containing compound can improve a deposition efficacy of the cooling sensate agent on surfaces of the oral cavity thereby providing long-lasting freshness in a cost-effective way. A N-substituted p-methanecarboxamide containing compound refers to a compound comprising a menthanecarboxamide functional group and the compound may comprise the following structure:

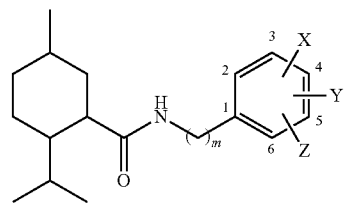

in which m is 0 or 1, Y and Z are selected independently from the group consisting of H, OH, C1-C4 straight or branched alkyl, and C1-C4 straight or branched alkoxy; X is (CH2)n-R, where n is 0 or 1 and R is a group with non-bonding electrons, with the provisos that:
  (a) When Y and Z are H, X is not F, OH, MeO or NO2 in the 4-position and is not OH in the 2 or 6-position;
  (b) When Y or Z is H then X, Y and Z are such that;
    (i) The groups in the 3- and 4-positions are not both Ome;
    (ii) The groups in the 4- and 5-positions are not both Ome;
    (iii) The groups in 3- and 5-positions are not OMe if the group in the 4-position is OH; and
    (iv) The groups in the 3- and 5-positions are not OH if the group in the 4-position is methyl Having the combination of the N-substituted p-methanecarboxamide containing compound and a calcium-containing abrasive based carrier enables a higher deposition level of the N-substituted p-methanecarboxamide containing compound on surfaces of the oral cavity relative to conventional compositions made up of a silica abrasive based carrier. Having a higher deposition level of the N-substituted p-methanecarboxamide containing compound exhibits a long-lasting cooling effect. Experimental results demonstrating the technical effect are described hereinbelow.

In the following description, the composition described is an oral care composition, such as a dentifrice composition for dental and oral hygiene care and to deliver a variety of benefits such as freshness and to provide protection against tooth decay and cavities. However, it is contemplated that the composition may be configured for use in a variety of applications to provide freshness in the oral cavity and the composition may include but is not limited to oral care products, such as, for example, dentifrice compositions, chewing gum, mints, breath fresheners in any form, dental implements, or other oral cavity materials, products or devices where a long-lasting cooling sensation is desired. A dental implement may include but is not limited to impregnated fibers including dental floss or tape, chips, strips, films and polymer fibers.

Prior to describing the present invention in detail, the following terms are defined for clarity. Terms not defined should be given their ordinary meaning as understood by a skilled person in the relevant art.

The term "orally acceptable carrier" as used herein means a suitable vehicle or ingredient, which can be used to form and/or apply the present compositions to the oral cavity in a safe and effective manner.

The term "effective amount" as used herein means an amount of a compound or composition sufficient to induce a positive benefit, an oral health benefit, and/or an amount low enough to avoid serious side effects, i.e., to provide a reasonable benefit to risk ratio, within the sound judgment of a skilled artisan.

The term "oral care composition" meaning that the composition provides a benefit when used in the oral cavity. The oral care composition of the present invention may be in various forms including toothpaste, dentifrice, tooth gel, sub gingival gel, foam, mousse, prophy paste, petrolatum gel, or denture adhesive. The oral care composition is in the form of a paste or gel. The oral care composition is in the form of a dentifrice. The oral care composition may also be incorporated onto strips or films for directing application or attachment to oral surfaces, or incorporated into floss.

The term "dentifrice" as used herein means paste, gel, powder, tablets, or liquid formulations, unless otherwise specified, that are used to clean the surfaces of the oral cavity. The term "teeth" as used herein refers to natural teeth as well as artificial teeth or dental prosthesis.

All percentages, parts and ratios are based upon the total weight of the compositions of the present invention, unless otherwise specified. All such weights as they pertain to listed ingredients are based on the active level and, therefore do not include solvents or by-products that may be included in commercially available materials, unless otherwise specified. The term "weight percent" may be denoted as "wt %" herein. All molecular weights as used herein are weight average molecular weights expressed as grams/mole, unless otherwise specified.

Composition

A composition according to the present invention should be configured to be suitable for use in the oral cavity of humans and comprises a calcium-containing abrasive based carrier including water and a calcium-containing abrasive, and a cooling sensate agent having a N-substituted p-menthanecarboxamide containing compound in a level of 0.002% to 0.006% by weight of the composition. A technical effect of a calcium-containing abrasive based carrier with the above level of a cooling sensate agent is that a higher deposition of the cooling sensate agent is deposited on surfaces of the oral cavity relative to a silica abrasive based carrier having the same level of cooling sensate agent. The calcium-containing abrasive based carrier may be formulated with high water (e.g. >45%) and high calcium-containing abrasive (e.g. >25%) to provide a cost-effective solution.

Optionally, the composition may be substantially free of a humectant. It is believed that being substantially free of humectant alters the way the cooling sensate agent can be released from the calcium-containing abrasive based carrier to reach the receptors.

Optionally, the composition of the present invention may include one or more optional components including but not limited to a fluoride ion source, a pH modifying agent, a humectant, a thickening system, PEG, an anti-calculus agent, a surfactant, and a flavorant to provide one or more benefits described hereinafter with reference to the respective component. The composition of the present invention may be a dentifrice composition comprising: 30% to 55%, by weight of the composition, of water; 25% to 50%, by weight of the composition, of a calcium-containing abrasive; 0.001% to 0.02% by weight of the composition of a N-substituted p-menthanecarboxamide containing compound, 0.0025% to 2%, by weight of the composition, of a fluoride ion source; 0% to 2%, by weight of the composition, of a humectant, wherein the humectant is selected from sorbitol, glycerol, or and a combination thereof; and wherein said composition has a pH greater than 7.8, preferably the pH is greater than 8, more preferably the pH is greater than 8.5. An advantage is the relatively cost effectiveness of the composition by having relatively high level of water and minimizing other ingredients including a N-substituted p-menthanecarboxamine containing compound, and humectant.

Components of a composition of the present invention are described in the following paragraphs.

Water

A composition of the present invention may comprise from 20% to 75%, by weight of the composition of total water. More specifically, the composition may include from 40% to 70%, from 45% to 65%, from 40% to 60%, from 50% to 70%, from 50% to 60%, from 45% to 55%, from 55% to 65%, from 50% to 60%, about 55%, or different combinations of the upper and lower percentages described above or combinations of any integer in the ranges listed above, of water by weight of the composition. The composition may be a dentifrice composition and comprise herein from 30% to 55%, from 30% to 55%, from 34% to 55%, from 35% to 55%, from 40% to 55%, or different combinations of the upper and lower percentages described above or combinations of any integer in the ranges listed above, of water by weight of the composition. Further, the dentifrice composition may comprise 34%, 38%, 40%, 42%, 44%, 46%, 48%, or 50%, by weight of the composition, of water. The water may be added to the formulation and/or may come into the composition from the inclusion of other ingredients.

Calcium-Containing Abrasive

A composition according to the present invention may comprise from 20% to 60% by weight of a calcium-containing abrasive, preferably wherein the calcium-containing abrasive is selected from the group consisting of calcium carbonate, dicalcium phosphate, tricalcium phosphate, calcium orthophosphate, calcium metaphosphate, calcium polyphosphate, calcium hydroxyapatite, and combinations of two or more of the compounds listed above. The composition preferably comprises from 25% to 60%, more preferably from 25% to 50%, even more preferably from 25% to 40%, yet even more preferably from 26% to 39%, from 27% to 47%, from 27% to 37%, from 30% to 35%, from 30% to 34%, or different combinations of the upper and lower percentages described above or combinations of any integer in the ranges listed above, of a calcium-containing abrasive by weight of the composition.

When the calcium-containing abrasive comprises calcium carbonate, the calcium carbonate may be selected from the group consisting of fine ground natural chalk, ground calcium carbonate, precipitated calcium carbonate, and combinations of two or more compounds listed above.

Fine ground natural chalk ("FGNC") is one of the more preferred calcium-containing abrasives useful in the present invention. It can be obtained from limestone or marble. FGNC may also be modified chemically or physically by coating during milling or after milling by heat treatment. Typical coating materials include magnesium stearate or oleate. The morphology of FGNC may also be modified during the milling process by using different milling techniques, for example, ball milling, air-classifier milling or spiral jet milling. The natural calcium carbonate may have a particle size of 325 to 800 mesh, a mesh selected from 325, 400 600, 800, or combinations thereof; the particle size is from 0.1 to 30 microns, from 0.1 to 20 microns, or from 5 to 20 microns The composition of the present invention may be free or substantially free of silicate.

Cooling Sensate Agent

The composition according to the present invention may include from 0.001% to 5%, from 0.001% to 0.02%, from 0.002% to 0.006%, from 0.002% to 0.004%, from 0.01% to 4%, from 0.1% to 3%, from 0.5% to 2%, 1% to 1.5%, 0.5% to 1%, by weight of the composition, or different combinations of the upper and lower percentages described above or combinations of any integer in the ranges listed above, of a cooling sensate agent comprising a N-substituted p-menthanecarboxamide containing compound. The N-substituted p-menthanecarboxamide containing compound may be selected from the group consisting of: N-ethyl-p-menthan-3-carboxamide, known commercially as "WS-3", and others in the series such as WS-5 (N-ethoxycarbonylmethyl-p-menthan-3-carboxamide), WS-12 [N-(4-methoxyphenyl)-p-menthan-3-carboxamide] and WS-14 (N-tert-butyl-p-menthane-3-carboxamide). Examples of menthane carboxy esters include WS-4 and WS-30. An example of a synthetic carboxamide coolant that is structurally unrelated to menthol is N,2,3-trimethyl-2-isopropylbutanamide, known as "WS-23". Additional examples of synthetic coolants include alcohol derivatives such as 3-(i-menthoxy)-propane-1,2-diol known as TK-10, isopulegol (under the tradename Coolact P) and p-menthane-3,8-diol (under the tradename Coolact 38D) all available from Takasago; menthone glycerol acetal known as MGA; menthyl esters such as menthyl acetate, menthyl acetoacetate, menthyl lactate known as Frescolat® supplied by Haarmann and Reimer, and monomenthyl succinate under the tradename Physcool from V. Mane.

Further, the N-substituted p-menthanecarboxamide containing compound may be selected from the group consisting of: N-(4-cyanomethylphenyl)-p-menthanecarboxamide, N-(4-sulfamoylphenyl)-p-menthanecarboxamide, N-(4-cyanophenyl)-p-menthanecarboxamide, N-(4-acetylphenyl)-p-menthanecarboxamide, N-(4-hydroxymethylphenyl)-p-menthanecarboxamide and N-(3-hydroxy-4-methoxyphenyl)-p-menthanecarboxamide. In particular, a technical effect of a N-substituted p-methanecarboxamide containing compound selected from the above group is it exhibits a long-lasting cooling effect due to the substitution at N-position with an aryl moiety bearing certain substituents.

Other N-substituted p-menthane carboxamide containing compounds may include amino acid derivatives including but not limited to, such as those disclosed in WO 2006/103401 and in U.S. Pat. Nos. 4,136,163; 4,178,459 and 7,189,760 such as N-((5-methyl-2-(1-methylethyl)cyclohexyl)carbonyl)glycine ethyl ester and N-((5-methyl-2-(1-methylethyl)cyclohexyl)carbonyl)alanine ethyl ester.

A technical effect of providing the N-substituted p-methanecarboxamide containing compound in a calcium containing abrasive based carrier is that the combination increases a deposition efficacy of the N-substituted p-methanecarboxamide containing compound on surfaces of the oral cavity. This effect is particularly evident with the cooling sensate agents designated as MGA, chemically menthone glycerol acetal and designated as G-180, chemically N-(4-cyanomethylphenyl)-p-menthanecarboxamide, supplied by Givaudan as a 7.5% solution in flavor oil such as spearmint or peppermint.

Sweetener

A composition of the present invention may include one or more sweetening agents. These include sweeteners such as saccharin, dextrose, sucrose, lactose, maltose, levulose, aspartame, sodium cyclamate, D-tryptophan, dihydrochalcones, acesulfame, sucralose, neotame, and mixtures thereof. Sweetening agents are generally used in an oral care composition at levels of from 0.005% to 5%, from 0.01% to 1%, from 0.1% to 0.5%, by weight of the composition, or different combinations of the upper and lower percentages described above or combinations of any integer in the ranges listed above.

Fluoride Ion Source

The composition may include an effective amount of an anti-caries agent to prevent caries. In one example, the anti-caries agent is a fluoride ion source. The fluoride ion may be present in an amount sufficient to give a fluoride ion concentration in the composition at 25° C., and/or can be used at levels of from 0.0025% to 5%, from 0.005% to 2.0%, by weight of the composition, or different combinations of the upper and lower percentages described above or combinations of any integer in the ranges listed above to provide anti-caries effectiveness. Representative fluoride ion sources include: stannous fluoride, sodium fluoride, potassium fluoride, amine fluoride, sodium monofluorophosphate, and zinc fluoride. In one example the dentifrice composition contains a fluoride source selected from stannous fluoride, sodium fluoride, and combinations thereof. The fluoride ion source may include sodium monofluorophosphate, and wherein the composition comprises 0.0025% to 2%, by weight of the composition, of the sodium monofluorophosphate, from 0.5% to 1.5%, from 0.6% to 1.7%, or different combinations of the upper and lower percentages described above or combinations of any integer in the ranges listed above. In another example, the composition comprises from 0.0025% to 2%, by weight of the composition, of a fluoride ion source. In one example, the composition of the present invention may have a dual fluoride ion source, specifically sodium monofluorophosphate and an alkaline metal fluoride. Without wishing to be bound by theory, such an approach may provide an improvement in mean fluoride uptake.

pH

The pH of the dentifrice composition may be greater than pH 7.8, preferably greater than pH 8, more preferably from greater than pH 8.0 to pH 11, yet more preferably from pH 8.5 to pH 11, yet still more preferably at or greater than pH 9 to pH 10.5. Preferably, the pH is from pH 9 to pH 10. The relatively high pH of the present inventive composition helps provide for fluoride stability. Without wishing to be bound theory, at below pH 8 calcium ion may bind with the fluoride. Thus, it is desirable to have the dentifrice composition have a greater than pH 8.0 to maximize the stability of the fluoride ion source. A method for assessing pH of dentifrice is described is below. For purposes of clarification, although the analytical method describes testing the dentifrice composition when freshly prepared, for purposes of claiming the present invention, the pH may be taken at any time during the product's reasonable lifecycle (including but not limited to the time the product is purchased from a store and brought to the user's home).

pH Modifying Agent

The dentifrice compositions herein may include an effective amount of a pH modifying agent, the pH modifying agent may be a pH buffering agent. The pH modifying agents, as used herein, refer to agents that can be used to adjust the pH of the dentifrice compositions to the above-identified pH range. The pH modifying agents may include alkali metal hydroxides, ammonium hydroxide, organic ammonium compounds, carbonates, sesquicarbonates, borates, silicates, phosphates, imidazole, and mixtures thereof. Specific pH agents include monosodium phosphate (monobasic sodium phosphate or "MSP"), trisodium phosphate (sodium phosphate tribasic dodecahydrate or "TSP"), sodium benzoate, benzoic acid, sodium hydroxide, potassium hydroxide, alkali metal carbonate salts, sodium carbonate, imidazole, pyrophosphate salts, sodium gluconate, lactic acid, sodium lactate, citric acid, sodium citrate, phosphoric acid. 0.01% to 3%, preferably from 0.1% to 1%, by weight of the composition, of TSP, and 0.001% to 2%, preferably from 0.01% to 0.3%, by weight of the composition, of monosodium phosphate may be used. Without wishing to be bound by theory, TSP and monosodium phosphate may also have calcium ion chelating activity and therefore provide some monofluorophosphate stabilization (in those formulations containing monofluorophosphate).

A method for assessing pH of dentifrice is described hereafter. The pH is measured by a pH Meter with Automatic Temperature Compensating (ATC) probe. The pH Meter is capable of reading to 0.001 pH unit. The pH electrode may be selected from one of the following (i) Orion Ross Sure-Flow combination: Glass body—VWR #34104-834/Orion #8172BN or VWR #10010-772/Orion #8172BNWP; Epoxy body—VWR #34104-830/Orion #8165BN or VWR #10010-770/Orion #8165BNWP; Semi-micro, epoxy body—VWR #34104-837/Orion #8175BN or VWR #10010-774/Orion #3175BNWP; or (ii) Orion PerpHect combination:VWR #34104-843/Orion #8203BN semi-micro, glass body; or (iii) suitable equivalent. The automatic temperature compensating probe is Fisher Scientific, Cat #13-620-16.

A 25% by weight slurry of dentifrice is prepared with deionized water, and thereafter is centrifuged for 10 minutes at 15000 rotations-per-minute using a SORVALL RC 28S centrifuge and SS-34 rotor (or equivalent gravitational force, at 24149 g force). The pH is assessed in supernatant after one minute or the taking reading is stabilized. After each pH assessment, the electrode is washed with deionized water. Any excess water is wiped with a laboratory grade tissue. When not in use, the electrode is kept immersed in a pH 7 buffer solution or an appropriate electrode storage solution.

Low Level or Free of Humectants

The compositions herein may contain a relatively low amount, or even be substantially free or free, of humectants. Non-limiting examples of humectant levels, by weight of the oral care composition, include 0.1%, 0.5%, 1%, 1.5%, 2%, or 0%. It is known that humectants function to prevent water loss from the composition. Without wishing to be bound by theory, the absence of humectant in the composition may alter the way the cooling sensate agent can be released to reach receptors at peripheral nerve fibers in surfaces of the oral cavity and have a positive effect on improving deposition efficacy of the cooling sensate agent on the surfaces of the oral cavity.

Preferably the dentifrice compositions of the present invention comprise from 0% to 2%, by weight of the composition, of a humectant, wherein the humectant is selected from sorbitol, glycerol, and combination thereof; more preferably the composition contain from 0% to 1.5%, yet more preferably 0% to 1%, yet still more preferably 0% to 0.5%, by weight of the composition of said humectant; from 0% to 0.1%; the composition is substantially free of the subject humectant.

The term "humectant," for the purposes of present invention, include edible polyhydric alcohols such as glycerin, sorbitol, xylitol, butylene glycol, propylene glycol, and combinations thereof. In one example, the humectant is a polyol, preferably wherein the polyol is selected from sorbitol, glycerin, and combinations thereof. In yet another example, the humectant is sorbitol. A potential advantage of having a dentifrice composition that contains low levels of humectant (i.e., at or less than 2 wt %), without wishing to be bound by theory, is those dentifrice compositions that are free of humectants such as glycerol or sorbitol may provide improved deposition efficacy of the cooling sensate agent as compared to those compositions having the high levels of such humectants. In one example, the dentifrice compositions of the present invention comprise from 0% to 2%, 0% to 1%, 0% to 0.5%, 0 wt % to 0.1 wt % by weight of the composition, of glycerin, sorbitol, or different combinations of the upper and lower percentages described above or combinations of any integer in the ranges listed above. The composition may be substantially free of both glycerin and sorbitol.

Thickening System

The dentifrice compositions of the present invention may comprise a thickening system. Preferably the dentifrice composition comprises from 0.5% to 4%, from 0.8% to 3.5%, from 1% to 3%, from 1.3% to 2.6%, by weight of the composition, of the thickening system. The thickening system may comprise a thickening polymer, a thickening silica, or a combination thereof. If the thickening system comprises a thickening polymer, the thickening polymer may be selected from a carboxymethyl cellulose, a linear sulfated polysaccharide, a natural gum, and combination thereof. If the thickening system comprises a thickening polymer, the thickening polymer may be selected from the group consisting of: (a) 0.01% to 3%, 0.1% to 2.5%, or 0.2% to 1.5% of a carboxymethyl cellulose ("CMC") by weight of the composition; (b) 0.01% to 2.5%, 0.05% to 2%, 0.1% to 1.5%, by weight of the composition, of a linear sulfated polysaccharide, preferably wherein the linear sulfated polysaccharide is a carrageenan; (c) 0.01% to 7%, 0.1% to 4%, from 0.1% to 2%, from 0.2% to 1.8%, by weight of the composition, of a natural gum; and (d) combinations thereof. The thickening system may comprise (a) 0.01% to 3%, 0.1% to 2.5%, more preferably 0.2% to 1.5% of a carboxymethyl cellulose ("CMC") by weight of the composition; (b) 0.01% to 2.5%, 0.05% to 2%, or 0.1% to 1.5%, by weight of the composition, of a linear sulfated polysaccharide, preferably wherein the linear sulfated polysaccharide is a carrageenan; and (c) a thickening silica.

When the thickening system comprises a thickening silica, the thickening silica may be from 0.01% to 10%, from 0.1% to 9%, or 1% to 8% by weight of the composition.

The linear sulfated polysaccharide may be a carrageenan (also known as carrageenin). Examples of carrageenan include Kappa-carrageenan, Iota-carrageenan, Lambda-carrageenan, and combinations thereof. The thickening silica may be obtained from sodium silicate solution by destabilizing with acid as to yield very fine particles. It will be appreciated by a person skilled in the art that silicas used as thickening silicas are different from silicas used as abrasive silicas. One commercially available example for use as thickening silicas is ZEODENT® branded silicas from Huber Engineered Materials (e.g., ZEODENT® 103, 124, 113 115, 163, 165, 167). Silicas suitable for use as abrasive silicas may include precipitated silica materials such as those marketed by the Huber Engineered Materials (e.g., ZEODENT®119, 118, 109, 129).

The CMC may be prepared from cellulose by treatment with alkali and monochloro-acetic acid or its sodium salt. Different varieties are commercially characterized by viscosity. One commercially available example is Aqualon™ branded CMC from Ashland Special Ingredients (e.g., Aqualon™ 7H3SF; Aqualon™ 9M3SF Aqualon™ TM9A; Aqualon™ TM12A).

A natural gum may be selected from the group consisting of gum karaya, gum arabic (also known as acacia gum), gum tragacanth, xanthan gum, and combination thereof. More preferably the natural gum is xanthan gum. Xanthan gum is a polysaccharide secreted by the bacterium *Xanthomonas camestris*. Generally, xanthan gum is composed of a pentasaccharide repeat units, comprising glucose, mannose, and glucuronic acid in a molar ratio of 2:2:1, respectively. The chemical formula (of the monomer) is $C_{35}H_{49}O_{29}$. The xanthan gum may be from CP Kelco Inc (Okmulgee, US).

Viscosity

When the composition of the present invention is a dentifrice composition, preferably the dentifrice composition has a viscosity range from 150,000 centipoise to 850,000 centipoise ("cP"). A method for assessing viscosity is described. The viscometer is Brookfield® viscometer, Model DV-I Prime with a Brookfield "Helipath" stand. The viscometer is placed on the Helipath stand and leveled via spirit levels. The E spindle is attached, and the viscometer is set to 2.5 RPM. Detach the spindle, zero the viscometer and install the E spindle. Then, lower the spindle until the crosspiece is partially submerged in the paste before starting the measurement. Simultaneously turn on the power switch on the viscometer and the helipath to start rotation of the spindle downward. Set a timer for 48 seconds and turn the timer on at the same time as the motor and helipath. Take a reading after the 48 seconds. The reading is in cP.

PEG

The compositions of the present invention may optionally comprise polyethylene glycol (PEG), of various weight percentages of the composition as well as various ranges of average molecular weights. The compositions may have from 0.1% to 5%, from 0.5% to 4%, from 1% to 3%, by weight of the composition, of PEG. The PEG may have a range of average molecular weight from 100 Daltons to 1600 Daltons, from 200 to 1000, from 400 to 800, from 500 to 700 Daltons. PEG is a water soluble linear polymer formed by the addition reaction of ethylene oxide to an ethylene glycol equivalent having the general formula is: $H-(OCH_2CH_2)_n-OH$. One supplier of PEG is Dow Chemical Company under the brandname of CARBOWAX™. Without wishing to be bound by theory, having some PEG in the dentifrice composition may help with physical stability.

Anti-Calculus Agent

The dentifrice compositions may include an effective amount of an anti-calculus agent, which may be present from 0.05% to 50%, from 0.05% to 25%, from 0.1% to 15% by weight of the composition, or different combinations of the upper and lower percentages described above or combinations of any integer in the ranges listed above. One example is a pyrophosphate salt as a source of pyrophosphate ion. The composition may comprise tetrasodium pyrophosphate (TSPP) or disodium pyrophosphate or combinations thereof, preferably 0.01% to 2%, more preferably from 0.1% to 1%, by weight of the composition, of the pyrophosphate salt. Without wishing to be bound by theory, TSPP may provide not only calcium chelating thereby mitigating plaque formation, but may also provide the additional benefit of monofluorophosphate stabilization (in those formulations containing monofluorophosphate).

Surfactant

The dentifrice compositions herein may include a surfactant. The surfactant may be selected from anionic, nonionic, amphoteric, zwitterionic, cationic surfactants, or mixtures thereof. The composition may include a surfactant at a level of from 0.01% to 10%, from 0.025% to 9%, from 0.05% to 5%, from 0.1% to 2.5%, from 0.5% to 2%, or from 0.1% to 1% by weight of the composition, or different combinations of the upper and lower percentages described above or combinations of any integer in the ranges listed above. The composition may comprise 0.1% to 5%, preferably 0.1% to 3%, from 0.3% to 3%, from 1.2% to 2.4%, from 1.2% to 1.8%, from 1.5% to 1.8%, by weight of the composition, or different combinations of the upper and lower percentages described above or combinations of any integer in the ranges listed above, of the anionic surfactant sodium lauryl sulfate ("SLS").

Flavorant (Flavor Composition)

The composition herein may comprise an additional flavor composition to improve user compliance to prescribed or recommended use of oral care products. In particular, it is believed that the combination of a flavor composition with a cooling sensate agent may provide an improved refreshing sensation with a well-rounded flavor profile.

The composition herein may include from about 0.001% to about 5%, from about 0.01% to about 4% from about 0.1% to about 3%, from about 0.5% to about 2%, 1% to 1.5%, 0.5% to 1%, or different combinations of the upper and lower percentages described above or combinations of any integer in the ranges listed above, of a flavor composition by weight of the composition. Excluded from the definition of flavor composition is "sweetener" (as described above).

Further examples of flavor compositions or flavor ingredients include: mint oils, wintergreen, clove bud oil, *cassia*, sage, parsley oil, marjoram, lemon, orange, propenyl guaethol, heliotropine, 4-cis-heptenal, diacetyl, methyl-p-tert-butyl phenyl acetate, methyl salicylate, ethyl salicylate, 1-menthyl acetate, oxanone, a-irisone, methyl cinnamate, ethyl cinnamate, butyl cinnamate, ethyl butyrate, ethyl acetate, methyl anthranilate, iso-amyl acetate, iso-amyl butyrate, allyl caproate, eugenol, eucalyptol, thymol, cinnamic alcohol, octanol, octanal, decanol, decanal, phenylethyl alcohol, benzyl alcohol, a-terpineol, linalool, limonene, citral, neral, geranial, geraniol nerol, maltol, ethyl maltol, anethole, dihydroanethole, carvone, menthone, beta-damascenone, ionone, gamma-decalactone, gamma-nonalactone, y-undecalactone, or combinations thereof. Generally suitable flavor ingredients are chemicals with structural features and functional groups that are less prone to redox reactions. These include derivatives of flavor ingredients that are saturated or contain stable aromatic rings or ester groups.

The flavor composition may comprise from 1% to 99% of menthol (e.g., L-Menthol) by weight of flavor composition, from 10% to 90%, or from 20% to 80%, or from 30% to 70%, or from 40% to 60%, or combinations thereof, of menthol by weight of the flavor composition.

The flavor composition may comprise from 1% to 99% of menthone (e.g., 1-Menthone) by weight of the flavor composition, from 0.5% to 50%, from 1% to 40%, from 2% to 30%, from 3% to 20%, from 4% to 15%, or different combinations of the upper and lower percentages described above or combinations of any integer in the ranges listed above, of menthol by weight of the flavor composition.

One non-limiting example of a flavorant composition is "Flavor A" as detailed in Table 3 of the Examples described hereinafter.

Method of Use

The composition according to the present invention may be formulated into an oral care product using known methods which will not be described. The oral care product may be selected from the group consisting of: toothpaste, dentifrice, tooth gel, sub gingival gel form, mousse, prophy paste, petrolatum gel, denture adhesive, strips and films for direct application or attachment to oral surfaces.

The composition of the present invention can be implemented in a method of increasing deposition of N-substituted p-menthylcarboxamide on a surface of an oral cavity by contacting the surface of the oral cavity with the composition of the present invention, preferably contacting surfaces includes brushing teeth. If the composition is comprised in a dental implement, contacting surfaces may include flossing teeth or direct application or attachment to oral surfaces.

The following examples are intended to more fully illustrate the present invention and are not to be construed as limitations of the present invention since many variations thereof are possible without departing from the scope of the present invention. All parts, percentages and ratios used herein are expressed as percent weight unless otherwise specified.

Examples

Test equipment/materials and test oral care compositions are first described under Materials, then Test Methods are provided, and lastly results are discussed. Data is provided demonstrating the oral care compositions of the present invention having improved deposition efficacy of a cooling sensate agent in the oral cavity. Equipment and materials used in the Test Methods described hereinafter are listed in Table 1 below. The formulations of inventive and comparative compositions are provided in Table 2 below. The compositions are prepared using conventional methods.

Materials

TABLE 1

| Equipment/Materials | |
|---|---|
| Component | Example |
| Substrate to simulate membranes in the oral cavity | Mammal skin |
| Equipment for Liquid chromatography-mass spectrometry (LC-MS) analysis | Supplier name: Waters Equipment Code: AB SCIEX 6500 LC-MS Software Version: Analyst 1.6.2 |
| Water Rinse | De-ionized Water |
| Artificial Saliva | A water solution containing 20 mM Sodium Hydrogen Carbonate (NaHCO$_3$), 2.75 mM Potassium Hydrogen Phosphate (K$_2$HPO$_4$), 12.20 mM Potassium dihydroizen phosphate (KH$_2$PO$_4$), 15 mM Sodium Chloride (NaCl) |
| Organic Solvent | Ethyl Acetate |

Table 2 describes six oral care compositions which are evaluated. Inventive Compositions A and B are inventive compositions while Comparative Compositions C, D, E, F are comparative compositions. Inventive Compositions A and B do not contain any silica abrasive while Comparative Compositions C, D, E, F contain silica abrasive (Silica 119 as an example).

TABLE 2

| Ingredients of Inventive and Control Compositions | | | | | | |
|---|---|---|---|---|---|---|
| Ingredients (by weight of the | Inventive Composition(s) | | Comparative Composition(s) | | | |
| composition (wt %)) | A | B | C | D | E | F |
| Added Water | 56.94% | 56.95% | 6.16% | 6.16% | 6.16% | 6.16% |
| Calcium carbonate | 31.04% | 31.04% | — | — | — | — |
| Silica 165 | 2.541% | 2.541% | — | — | — | — |
| Silica 119 | — | — | 16.00% | 16.00% | 16.00% | 16.00% |
| Sorbitol Solution 70% | — | — | 66.54% | 66.54% | 66.54% | 66.54% |
| ((1R,2S,5R)-N-(4-(cyanomethyl)phenyl)-p-menthanecarboxamide, (available as G-180 from Givaudan) | 0.01% | 0.004% | 0.01% | 0.006% | 0.004% | 0.006% |
| CMC | 0.89% | 0.89% | 0.70% | 0.70% | 0.70% | 0.70% |
| linear sulfated polysaccharide (Carrageenan 1280) | 1.164% | 1.164% | — | — | — | — |
| Carbomer | — | — | 0.22% | 0.22% | 0.22% | 0.22% |
| Sodium Fluoride | — | — | 0.243% | 0.243% | 0.243% | 0.243% |
| Sodium monofluorophosphate | 1.067% | 1.067% | — | — | — | — |
| Tetrasodium pyrophosphate | 0.582% | 0.582% | — | — | — | — |
| Monobasic sodium phosphate | 0.078% | 0.078% | 0.40% | 0.40% | 0.40% | 0.40% |
| Trisodium phosphate | 0.407% | 0.407% | 0.93% | 0.93% | 0.93% | 0.93% |
| Sodium lauryl sulfate 29% solution | 3.880% | 3.880% | 7.50% | 7.50% | 7.50% | 7.50% |
| Sodium saccharin | 0.300% | 0.300% | 0.300% | 0.300% | 0.300% | 0.300% |
| Propylparaben | 0.049% | 0.049% | — | — | — | — |
| Methylparaben | 0.049% | 0.049% | — | — | — | — |
| Flavor A of Table 3 | 1.000% | 1.000% | 1.000% | 1.000% | 1.000% | 1.000% |
| | 100% | 100% | 100% | 100% | 100% | 100% |
| pH | 5.5 to 10.0 or | 5.5 to 10.0 or | 6.7 to 7.5 | 6.7 to 7.5 | 6.7 to 7.5 | 6.7 to 7.5 |

TABLE 2-continued

Ingredients of Inventive and Control Compositions

| Ingredients (by weight of the composition (wt %)) | Inventive Composition(s) | | Comparative Composition(s) | | | |
|---|---|---|---|---|---|---|
| | A | B | C | D | E | F |
| Total Water Content (including water from Sorbitol and SLS solutions) | 8.0 to 10.0 59.70% | 8.0 to 10.0 59.71% | 31.45% | 31.45% | 31.45% | 31.45% |

The pH value of each of the respective compositions are indicated in the above as target pH ranges and the respective pH value can be measured using the pH measurement method described hereinbefore. Flavor A used in the above compositions is a flavorant composition comprising the following components and weight percentages relative to the flavorant composition as detailed in Table 3 below.

TABLE 3

Flavorant Composition (Flavor A)

| Flavor Ingredient | Chemical name | Weight Percent |
|---|---|---|
| trans-Anethole | 1-Methoxy-4-((E)-1-propenyl)-benzene | 11% |
| 1-Menthone | (2S,5R)-5-methyl-2-propan-2-ylcyclohexan-1-one | 11.5% |
| Menthone | 5-methyl-2-propan-2-ylcyclohexan-1-one | 5.6% |
| L-Menthol | (1R,2S,5R)-5-methyl-2-propan-2-ylcyclohexan | 51% |
| (+)-Neomenthol | (1S,2S,5R)-5-methyl-2-propan-2-ylcyclohexan-1-ol | 0.5% |
| Eucalyptol | 4,7,7-trimethyl-8-oxabicyclo[2.2.2]octane | 14% |
| trans-3-Hexenyl iso-Valerate | hex-3-enyl 3-methylbutanoate | 0.3% |
| dl-Menthyl Acetate | (5-methyl-2-propan-2-ylcyclohexyl) acetate | 2% |
| Remaining ingredients which are not disclosed by the manufacturer | — | 4% |
| | Weight Percentage Total: | 100% |

Test Methods

A. Cooling Sensate Agent Deposition Test Method

This test method is to detect deposition of G-180 as an example of a cooling sensate agent on individual substrates treated with Inventive Composition A and Comparative Composition C respectively. The test method is performed under the following test conditions: at an average temperature of 20° C. to 24° C. and an average % relative humidity of 30% to 60%. The steps for performing the test include:

Step 1: Treat a set of substrates with Inventive Composition A to form Inventive Samples A1, A2, A3, A4, A5, A6, A7, A8, and A9. Treating another set of substrates with Comparative Composition C to form Comparative Samples C1, C2, C3, C4, C5, C6 and C7.

Step 2: Apply Inventive Samples A1, A2, A3, A4, A5 and A6 with water rinse to simulate a scenario of just after brushing with Inventive Composition A.

Step 3: Apply Inventive Samples A7, A8 and A9 with artificial saliva to simulate a scenario of 10 minutes of having the Inventive Composition A deposited within the oral cavity after brushing with the Inventive Composition A.

Step 4: Repeat Step 2 for Comparative Samples C1, C2, C3 and C4.

Step 5: Repeat Step 3 for Comparative Samples C5, C6 and C7.

Step 6: Extract substrate surfaces for Inventive Samples A1 to A9 and Comparative Samples C1 to C7 respectively by an organic solvent to form Extraction Solutions of the Inventive and Comparative Samples respectively.

Step 7: Determine a concentration level of G180 in each of Extraction Solutions by LC-MS analysis using the LC-MS equipment and software described in Table 1.

Step 8: Calculate an average of the concentration levels of G-180 in the Extraction Solutions of the Inventive Samples from Step 7 to generate an average concentration level of G180 deposited on a substrate treated with the Inventive Composition A.

Step 9: Calculate an average of the concentration levels of G-180 in the Extraction Solutions of the Comparative Samples from Step 7 to generate an average concentration level of G180 deposited on a substrate treated with the Comparative Composition C.

B. Coolness Effect Sensory Test Method

This test method is to evaluate the coolness effect of an inventive composition and a comparative composition. A so called Paired Comparison Brush Test Method ("Paired Comparison") is described. The method is essentially a reapplication of China GB 12310-90 (effective since 1990 Dec. 1), and ISO 5495-1983, titled "Sensory Analysis Methodology-Paired Comparison Test," (1983). Inventive Composition B and Comparative Compositions D, E, F are evaluated.

12 highly trained human panelists are recruited to evaluate Inventive Composition B and Comparative Composition D in randomized order as "Paired Comparison 1". 13 human panelists are recruited to evaluate Comparative Composition E and Comparative Composition F in randomized order as "Paired Comparison 2". The test method is performed under the following test conditions: at an average temperature of 20° C. to 22° C. and an average % relative humidity of 35% to 50%. The test method is carried out for each of the panelists according to the following steps:

Step 1: The panelist rinses his/her mouth three times with room temperature tap water, clean mouth cavity with toothbrush to remove the food debris.

Step 2: A toothbrush is dosed with 1.2 g of Inventive Composition B of Paired Comparison 1.

Step 3: The dosed toothbrush is dipped into tap water, and is gently tapped once to remove excess water.

Step 4: The panelist is instructed to use the same brushing habit that the panelist conducts at home for 1 minute.

Step 5: After Step 4, the panelist expectorates the Inventive Composition B and foam from his/her mouth into a sink, evaluate and record the cooling intensity.

Step 6: The panelist rinses his/her mouth with 30 ml of room temperature tap water.

Step 7: The panelist is asked to record the cooling intensity at different time points up to 25 minutes. No food and drink allowed during 25-minute test.

Step 8: After Step 7, the panelist is allowed to rest and eats a plain cracker to remove any residual taste of the Inventive Composition B.

Step 9: The panelist repeats Steps 1 to 7 with Comparative Composition D of Paired Comparison 1.

Step 10: The panelist is asked to rank Inventive Composition B and Comparative Composition D by answering the comparison questions at each designed time point up to 25 minutes: "Inventive Composition B has a stronger cooling effect", "Comparative Composition D has a stronger cooling effect", "Inventive Composition B and Comparative Composition D have the same cooling effect".

Step 11: A significance difference is calculated for Paired Comparison 1 based on standard statistical analysis methods at 90% confidence level and collated in Table 6. Such statistical analysis methods are known to the skilled person.

Steps 1 to 11 are repeated for Paired Comparison 2, and the significant difference is collated in Table 7.

Example I

Inventive Composition A and Comparative Composition C of Table 2 are evaluated according to the Cooling Sensate Agent Deposition Test Method described hereinbefore under Test Methods.

Table 4 below shows concentration results of the cooling sensate agent (for example, G180) in each of Extraction Solutions of Inventive Samples A1 to A6 and Comparative Samples C1 to C4 measured at a simulated time point (0 minutes) which demonstrate that Inventive Composition A has a higher concentration of G-180 deposited thereon relative to Comparative Composition C just after brushing.

TABLE 4

G-180 Deposition at simulated time point 0 minute

| Extraction Solution of Inventive Sample A | Amount of G180 (ng/cm$^2$) deposited on Substrate(s) after treating with Inventive Composition A at stimulated time point—0 minute | Extraction Solution of Comparative Sample C | Amount of G180 (ng/cm$^2$) deposited on Substrate(s) after treating with Comparative Composition C at stimulated time point—0 minute |
|---|---|---|---|
| A1 | 257.1 | C1 | 156.9 |
| A2 | 179.6 | C2 | 184.9 |
| A3 | 232.5 | C3 | 168.0 |
| A4 | 199.1 | C4 | 123.7 |
| A5 | 259.3 | — | — |
| A6 | 299.6 | — | — |
| Average | 237.8 | Average | 158.4 |

Specifically, Inventive Sample A shows a higher average concentration level (237.8 ng/cm$^2$) of G-180 deposited on the substrate relative to Comparative Sample C (average concentration level of 158.4 ng/cm2) after brushing at a stimulated time point of 0 minutes.

Table 5 below shows concentration results of the cooling sensate agent (for example, G180) in each of Extraction Solutions of Inventive Samples and Comparative Samples measured at a simulated time point (10 minutes) which demonstrate that Inventive Composition A has a higher concentration of G-180 deposited thereon relative to Comparative Composition C just after brushing.

TABLE 5

G-180 Deposition at simulated time point 10 minutes

| Extraction Solution of Inventive Sample A | Amount of G180 (ng/cm$^2$) deposited on Substrate(s) after treating with Inventive Composition A at stimulated time point—10 minutes | Extraction Solution of Comparative Sample C | Amount of G180 (ng/cm$^2$) deposited on Substrate(s) after treating with Comparative Composition C at stimulated time point—10 minutes |
|---|---|---|---|
| A7 | 181.7 | C5 | 141.5 |
| A8 | 217.7 | C6 | 136.8 |
| A9 | 224.2 | C7 | 117.7 |
| Average | 207.9 | Average | 132 |

Specifically, Inventive Sample A shows a higher average concentration level (207.9 ng/cm$^2$) of G-180 deposited on the substrate relative to Comparative Sample C (average concentration level of 132 ng/cm2) after brushing at a stimulated time point of 10 minutes.

Overall, the above results show that an oral care composition comprising high levels of water and calcium containing abrasive with G-180 in a predetermined amount has a higher G-180 deposition efficiency relative to a comparative oral care composition without the high levels of water and calcium containing abrasive and having a silicate abrasive based carrier material with G-180 in the same predetermined amount in both scenarios, i.e. before brushing and after brushing.

Further, the results in Tables 4 and 5 demonstrate that an oral care composition of the present invention provide an average concentration level of G-180 deposition within a range of 200 ng/cm$^2$ to 250 ng/cm$^2$ at 0 minutes or at 10 minutes. In contrast, comparative compositions provide a lower average concentration level of G-180 deposition within a range of 100 ng/cm$^2$ to 160 ng/cm$^2$ at 0 minutes or at 10 minutes.

Having a higher G-180 deposition efficiency on a surface of the oral cavity means that the use of the G-180 is optimized in a calcium containing abrasive based carrier as less G-180, without wishing to be bound by theory, is rinsed away during rinsing after brushing. As a result, there is more G-180 to provide an improved coolness effect relative to the comparative oral care composition which is demonstrated under Example II described hereinafter.

Example II

Table 6 shows results of Paired Comparison 1 in which Inventive Composition B and Comparative Composition D are evaluated according to the Coolness Effect Sensory Test described hereinbefore under Test Methods.

TABLE 6

Results of Paired Comparison 1

| Time (among 12 panelists) | Inventive Composition B has a stronger cooling effect | Comparative Composition D has a stronger cooling effect | Same cooling effect | Significant difference @ 90% confidence level? |
|---|---|---|---|---|
| @ 1 min (before brushing) | 8 | 3 | 1 | No |
| 2 minutes after rinse | 5 | 5 | 2 | No |
| 5 minutes after rinse | 4 | 6 | 2 | No |

TABLE 6-continued

Results of Paired Comparison 1

| Time (among 12 panelists) | Inventive Composition B has a stronger cooling effect | Comparative Composition D has a stronger cooling effect | Same cooling effect | Significant difference @ 90% confidence level? |
|---|---|---|---|---|
| 8 minutes after rinse | 3 | 7 | 2 | No |
| 10 minutes after rinse | 3 | 8 | 1 | No |
| 15 minutes after rinse | 2 | 8 | 2 | No |
| 20 minutes after rinse | 2 | 8 | 2 | No |
| 25 minutes after rinse | 3 | 8 | 1 | No |

The above results show that there is no significant difference in cooling effect between Inventive Composition B and Comparative Composition D based on statistical analysis at 90% confidence level. Inventive Composition B differs from Comparative Composition D mainly in that Inventive Composition B has a calcium containing abrasive based carrier while Comparative Composition D has a silica abrasive based carrier. Further, an amount of the cooling sensate agent (G-180) in Inventive Composition B is 0.002% (20 ppm) less than an amount of the cooling sensate agent (G-180) in Comparative Composition D. This means a higher level of the cooling sensate agent (G-180) is required in a silicate abrasive based composition to achieve a similar cooling effect. In contrast, a lower level of the cooling sensate agent (G-180) in a calcium abrasive based composition can achieve the same cooling effect thereby resulting in lower ingredient costs and enabling manufacture of a cost-effective oral care product. The above results demonstrate that having water, a calcium-containing abrasive and a cooling sensate agent comprising a N-substituted p-methanecarboxamide containing compound comprised in an oral care composition according to the present invention is effective in increasing deposition of the cooling sensate agent on surfaces of the oral cavity thereby improving longevity of freshness.

Table 7 shows results of Paired Comparison 2 in which Comparative Compositions E and F (both having silica abrasive based carrier with G-180, reference to Table 2) are evaluated according to according to the Coolness Effect Sensory Test described hereinbefore under Test Methods.

TABLE 7

| Time (among 13 panelists) | Comparative Composition E has a stronger cooling effect | Comparative Composition F has a stronger cooling effect | Same Cooling Effect | Significant difference @ 90% confidence level? |
|---|---|---|---|---|
| @ 1 min (before brushing) | 6 | 7 | 0 | No |
| 2 minutes after rinse | 5 | 7 | 1 | No |
| 5 minutes after rinse | 5 | 7 | 1 | No |
| 8 minutes after rinse | 5 | 7 | 1 | No |
| 10 minutes after rinse | 5 | 8 | 0 | No |
| 15 minutes after rinse | 5 | 8 | 0 | No |
| 20 minutes after rinse | 3 | 8 | 2 | No |
| 25 minutes after rinse | 2 | 10 | 1 | Yes |

The above results show that Comparative Composition F has a stronger cooling effect relative to Comparative Composition E based on >90% confidence level. Referring to Table 2, Comparative Composition F differs from Control Composition E in that a cooling sensate agent in Comparative Composition F is 0.002% more than an amount of the cooling sensate agent in Control Composition E. This demonstrates that an oral care composition having the combination of G-180 and silica-abrasive based carrier will require a higher amount of G-180 to provide improved freshness thereby increasing costs of the oral care composition.

Accordingly, it is beneficial to have water, a calcium-containing abrasive and a cooling sensate agent comprising a N-substituted p-methanecarboxamide containing compound comprised in an oral care composition according to the present invention because it is effective in increasing deposition of the cooling sensate agent on surfaces of the oral cavity thereby improving longevity of freshness while providing a cost-effective product.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral care composition comprising:
    (a) 20% to 75% by weight of the composition of water;
    (b) 20% to 60% by weight of the composition of a calcium-containing abrasive;
    (c) 0.001% to 0.02% by weight of the composition of a cooling sensate agent comprising a N-substituted p-menthanecarboxamide containing compound; and
    (d) 0% to 2% by weight of the composition of humectant.

2. The composition of claim 1, wherein the N-substituted p-methanecarboxamide containing compound is in an amount of 0.002% to 0.006%, by weight of the composition.

3. The composition of claim 1, wherein the water is in an amount of 40% to 70% by weight of the composition.

4. The composition of claim 1, wherein the composition further comprises:
    (a) 30% to 55% by weight of the composition of water;
    (b) 25% to 50% by weight of the composition of the calcium-containing abrasive;
    (c) 0.0025% to 2% by weight of the composition of a fluoride ion source; and
    (d) 0% to 1.5% by weight of the composition of humectant selected from sorbitol, glycerol, or a combination thereof; and wherein the composition has a pH greater than 7.8.

5. The composition of claim 4, wherein the composition is substantially free of the humectant.

6. The composition of claim 4, wherein the composition comprises from 0.2% to 1.5%, by weight of the composition, of the fluoride ion source.

7. The composition of claim 1, wherein the N-substituted p-menthycarboxamide containing compound is selected from the group consisting of: N-(4-cyanomethylphenyl)-p-menthanecarboxamide; N-(4-sulfamoylphenyl)-p-menthanecarboxamide; N-(4-cyanophenyl)-p-menthanecarboxamide; N-(4-acetylphenyl)-p-menthanecarboxamide, N-(4-hydroxymethylphenyl)-ρ-menthanecarboxamide; and N-(3-hydroxy-4-methoxyphenyl)-p-menthanecarboxamide.

8. The composition of claim 1, wherein the calcium-containing abrasive is selected from the group consisting of fine ground natural chalk, ground calcium carbonate, precipitated calcium carbonate and combinations thereof.

9. The composition of claim 1, further comprising 0.001% to 5% of a flavorant composition by weight of the composition, wherein the flavorant composition comprises at least one flavor ingredient selected from the group consisting of: 1-Methoxy-4-((E)-1-propenyl)-benzene, (2 S,5R)-5-methyl-2-propan-2-ylcyclohexan-1-one, 5-methyl-2-propan-2-ylcyclohexan-1-one, (1R,2S,5R)-5-methyl-2-propan-2-ylcyclohexan, (1 S,2S,5R)-5-methyl-2-propan-2-ylcyclohexan-1-ol, 4,7,7-trimethyl-8-oxabicyclo[2.2.2]octane, hex-3-enyl 3-methylbutanoate, and (5-methyl-2-propan-2-ylcyclohexyl)acetate.

10. The composition of claim 1, wherein the composition comprises from 0.1% to 5%, by weight of the composition, of polyethylene glycol.

11. The composition according to claim 1, further comprising a thickening system, wherein the thickening system further comprises a thickening polymer, a thickening silica, or a combination thereof.

12. The composition according to claim 11, wherein the thickening system comprises a thickening silica, wherein the thickening silica is from 0.01% to 10%, by weight of the composition.

13. The composition according to claim 1, wherein the composition is a dentifrice composition and wherein the N substituted p-menthanecarboxamide containing compound is present in an effective amount by weight of the composition to provide an average concentration level of at least 200 ng/cm$^2$ of the N-substituted p-menthanecarboxamide containing compound deposited on a surface of the oral cavity upon use.

14. The composition of claim 13, wherein the N-substituted p-methanecarboxamide containing compound is in an amount of 0.001% to 0.02%, by weight of the composition.

15. The composition of claim 13, wherein the water is in an amount of 40% to 70% by weight of the composition.

16. The composition of claim 13, wherein the composition further comprises:
   30% to 55% by weight of the composition of water;
   25% to 50% by weight of the composition of the calcium-containing abrasive;
   0.0025% to 2% by weight of the composition of a fluoride ion source, wherein the fluoride ion source is sodium monofluorophosphate; and
   0% to 1.5% by weight of the composition of a humectant, wherein the humectant is selected from sorbitol, glycerol, or a combination thereof; and wherein the composition has a pH greater than 7.8.

17. The composition of claim 13, wherein the N-substituted p-menthycarboxamide containing compound is selected from the group consisting of: N-(4-cyanomethylphenyl)-p-menthanecarboxamide; N-(4-sulfamoylphenyl)-p-menthanecarboxamide; N-(4-cyanophenyl)-p-menthanecarboxamide; N-(4-acetylphenyl)-p-menthanecarboxamide, N-(4-hydroxymethylphenyl)-ρ-menthanecarboxamide and N-(3-hydroxy-4-methoxyphenyl)-p-menthanecarboxamide.

18. The composition of claim 13, wherein the calcium-containing abrasive is selected from the group consisting of fine ground natural chalk, ground calcium carbonate, precipitated calcium carbonate and combinations thereof.

19. A method of increasing deposition of N-substituted p-menthylcarboxamide on a surface of an oral cavity, the method comprising the step of: contacting the surface of the oral cavity with an oral care composition according to claim 1.

20. The composition of claim 1, wherein the N-substituted p-menthycarboxamide containing compound is N-(4-cyanomethylphenyl)-p-menthanecarboxamide.

21. The composition of claim 4, wherein the fluoride ion source is sodium monofluorophosphate.

22. The composition of claim 11, wherein the thickening polymer is selected from the group consisting of: a carboxymethyl cellulose, a linear sulfated polysaccharide, a natural gum, and combinations thereof.

* * * * *